US012729362B2

(12) United States Patent
Peyser et al.

(10) Patent No.: US 12,729,362 B2
(45) Date of Patent: Sep. 8, 2026

(54) HOLLOW FIBER SCREENING TOOL, SYSTEM, AND METHOD

(71) Applicant: Repligen Corporation, Waltham, MA (US)

(72) Inventors: James Peyser, Billerica, MA (US); Michael Bransby, Altadena, CA (US); Philip Yuen, Long Beach, CA (US)

(73) Assignee: Repligen Corporation, Waltham, MA (US)

(*) Notice: Subject to any disclaimer, the term of this patent is extended or adjusted under 35 U.S.C. 154(b) by 974 days.

(21) Appl. No.: 17/936,426

(22) Filed: Sep. 29, 2022

(65) Prior Publication Data

US 2023/0098953 A1 Mar. 30, 2023

Related U.S. Application Data

(60) Provisional application No. 63/250,625, filed on Sep. 30, 2021.

(51) Int. Cl.
*C12M 1/00* (2006.01)
*G01N 15/08* (2006.01)

(52) U.S. Cl.
CPC ............ *C12M 29/04* (2013.01); *G01N 15/08* (2013.01); *G01N 2015/084* (2013.01)

(58) Field of Classification Search
None
See application file for complete search history.

(56) References Cited

U.S. PATENT DOCUMENTS

| | | | | |
|---|---|---|---|---|
| 5,601,757 | A * | 2/1997 | Biselli | C12M 29/04 261/122.1 |
| 9,446,354 | B2 * | 9/2016 | Shevitz | C12M 29/16 |
| 2009/0286296 | A1 * | 11/2009 | Hickey | C12M 29/16 435/41 |
| 2009/0311777 | A1 * | 12/2009 | Edwards | C12M 29/16 435/297.2 |
| 2017/0002305 | A1 * | 1/2017 | Shevitz | B01D 61/58 |
| 2017/0106341 | A1 * | 4/2017 | Labib | B01D 61/28 |
| 2018/0066219 | A1 * | 3/2018 | Borenstein | G01N 1/34 |
| 2019/0337979 | A1 * | 11/2019 | Bransby | C07K 1/36 |

* cited by examiner

*Primary Examiner* — Michael A Marcheschi
*Assistant Examiner* — Ashley Lopezlira
(74) *Attorney, Agent, or Firm* — KDW Firm PLLC

(57) ABSTRACT

A filter screening tool, system, and method allowing high throughput screening of filters (such as hollow fiber filters), such as for use in bioprocessing workflows. Feed material may be fed through different filter modules to assess, measure, analyze, determine, evaluate, teste, compare, screen, etc., properties or characteristics, etc., of filters within the filter modules. Each filter module may house a different type (e.g., material or configuration) of filter so that different filters may be compared and screened, such as for a selected use.

12 Claims, 7 Drawing Sheets

162
160
200
104
102
114
230
118
116
134
210
220
150
220d
224d
126d
222d
214d
232d
220c
224c
126c
214c
232c
220b
224b
126b
222b
214b
232b
220a
224a
222a
126a
214a
232a

HOLLOW FIBER SCREENING TOOL, SYSTEM, AND METHOD

CROSS-REFERENCE TO RELATED APPLICATIONS

This is a non-provisional of pending U.S. provisional patent application Ser. No. 63/250,625, filed Sep. 30, 2021, the entirety of which application is incorporated by reference herein.

FIELD

The present disclosure relates generally to the field of filters and filtration systems. In particular, the present disclosure relates to tools, systems, and methods for screening filters, such as hollow fiber filters.

BACKGROUND

Filtration is typically performed to separate, clarify, modify, and/or concentrate a solution, mixture, or suspension. In the biotechnology and pharmaceutical industries, filtration is vital for the successful production, processing, and testing of new drugs, diagnostics, chemicals, and other biological products (e.g., antibodies, including monoclonal antibodies; proteins, including recombinant proteins; vaccines; viral vectors, etc.). For example, in the process of manufacturing biologicals using cell cultures (animal, plant, bacteria, virus, etc.), filtration is performed for clarification, selective removal, and concentration of certain constituents from the culture media, or to modify the media prior to further processing. Filtration may also enhance productivity in high density cell perfusion cultures.

Filtration systems are commonly used with cell cultures grown in bioreactors. Bioreactors have been used for decades to carry out various processes involving cell growth, organisms (e.g., microorganisms) or biochemically active substances derived from such organisms. Various cell culture processes, such as batch, fed-batch, or continuous (including perfusion) processes, have been used for decades to grow cells in bioreactors. In the perfusion method for growing cells, culture medium, whose nutrients have been consumed and which contains increased levels of harmful waste products, is continuously removed from the culture and replaced with fresh medium. The constant addition and replenishment of fresh medium and continuous removal of waste products provides the cells with the nutrients it requires to achieve high cell concentrations. In general, the cells in the culture system create the protein or proteins of interest, or other products of interest (e.g., nucleotides, metabolites, antibodies, etc.), which are removed (such as in a typically cell-free harvest commonly referenced as permeate) via a filtration system. The remaining cell culture suspension (commonly referenced as retentate) is returned to the bioreactor. Various filtration systems have been used to keep the cells in the bioreactor system while allowing the spent media or products of interest to be removed.

Several specialized filters and filtration methods have been developed to separate materials according to their chemical and physical properties. Filters which have been developed in the art include flat surface filters, pleated filters, multi-unit cassettes, and tubular forms such as hollow fibers. However, when used to filter cell culture suspension or other biological fluids, such filters may clog with dead cells, cell debris, aggregates, or other constituents of the feed material. As the feed material is recirculated, if the filters have fouled or clogged, pathogens and other products may be retained in the feed material.

Various filtration systems, such as tangential flow filtration systems (also known as cross flow filtration or TFF), frequently utilize filters comprising one or more tubular filtration elements, such as hollow-fibers or tubular membranes. Where tubular filtration elements are used, they are typically packed together within a larger fluid vessel or housing to form a filter module. The housings generally are engineered to handle high pressures, and are placed in fluid communication at one end with a feed, and at the other end with a vessel or fluid path for the retentate. The permeate flows through pores in the walls of the fibers into the spaces between the fibers and within the larger fluid vessel. Tubular filtration elements provide large and uniform surface areas relative to the feed material volumes they can accommodate, and TFF systems utilizing these elements may be scaled easily from development to commercial scale. Despite their advantages, TFF systems filters may foul when filter flux limits are exceeded, and TFF systems have finite process capacities. Efforts to increase process capacities for TFF systems are complicated by the relationship between filter flux and fouling.

There is a need for improved filter materials which may be used for a greater number of runs through the filtering circuit. Various fiber chemistries and sizes are available, with different efficacies. Moreover, different filter materials may be useful in different applications, some filter materials performing differently or better in certain applications with other filter materials performing differently or better in other applications. For instance, protein therapeutics behave differently for each filter type depending on cell types and process conditions. However, current screening processes for filter materials are time consuming and can be costly. Moreover, current screening processes have inherent flaws, as different feedstreams are fed through different samples, and it is generally not possible to determine if differences in the samples are caused by the bioreactor or by variations in the cell culture passing through the filter module or by the filter module itself. Accordingly, there is a need for high throughput (HT) screening tools and systems and method for research and development (R&D), pharmacodynamics (PD), and manufacturing science and technology (MSAT) unit operations in bioprocessing workflows. In particular, hollow fiber tangential flow high throughput screening is a gap in the industry.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a filter tool is provided a screening tool for screening a plurality of different filters. The screening tool includes two or more filter modules, each filter module having a unique filter different from a filter of another filter module of the screening tool. Feed material flows through each filter module in parallel flow paths through the two or more filter modules.

In some embodiments, each filter module has fewer than ten hollow fiber filters, the hollow fiber filters of each filter module differing from the hollow fiber filters of another filter module of the screening tool. In some embodiments, each filter module has no more than three hollow fiber filters.

In some embodiments, the screening tool further includes at least one sensor associated with each filter module, the at least one sensor being selected from the group including of: a pressure sensor, a conductivity sensor, a temperature sensor, a flow sensor, an ultraviolet sensor, a turbidity sensors, and/or a combination thereof.

In some embodiments, the screening tool further includes a common inlet for the feed material and a common outlet for retentate. In some embodiments, the screening tool further includes a common outlet for permeate.

In some embodiments, the screening tool further includes a manifold having a first endcap and a second endcap, each filter module having a first end coupled to the first endcap and a second end coupled to the second endcap. In some embodiments, at least one of the first and second endcaps includes one or more connectors, each configured for coupling with a different one of the filter modules. In some embodiments, at least one of the filter modules includes a connector on at least one end thereof for coupling with an endcap connector.

In some embodiments, the method includes sensing at least one property of permeate flowing through the at least one filter of each of the filter modules.

In some embodiments, each filter module includes a different filter, the method further including comparing the at least one property of the different filters of the different filter modules to screen the different filters.

In some embodiments, the method further includes driving feed material through each filter module at substantially the same rate.

In accordance with various principles of the present disclosure, a method of screening different fiber materials includes introducing feed material into a screening tool; splitting the flow of the feed material into at least two flow paths, feeding feed material in each of the at least two flow paths into a different filter module, driving the feed material through at least one filter within each filter module, and sensing at least one property of the filters of the different filter modules.

In accordance with various principles of the present disclosure, a filter screening system includes a feed reservoir; a screening tool fluidly coupled with the feed reservoir and including at least two filter modules, and a sensor coupled to each of the at least two filter modules, where: each filter module includes a housing with a filter therein, and each filter module is configured to be coupled to a pump configured to drive feed material through the filter within each filter module.

In some embodiments, the feed reservoir includes a bioreactor. In some embodiments, the filter screening system further includes a filtration system in fluid communication with the bioreactor.

In some embodiments, the filter screening system further includes a sensor controller programmed to compare data from each sensor coupled to each of the at least two filter modules.

In some embodiments, the filter screening system further includes a pump coupled to each filter module to drive feed material through the filter within each filter module.

In some embodiments, the filter screening tool further including a multi-channel pump, each channel coupled to a different filter module.

In some embodiments, the filter within each of the at least two filter modules is a hollow fiber filter different from the hollow fiber filter within the other of the at least two filter modules.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
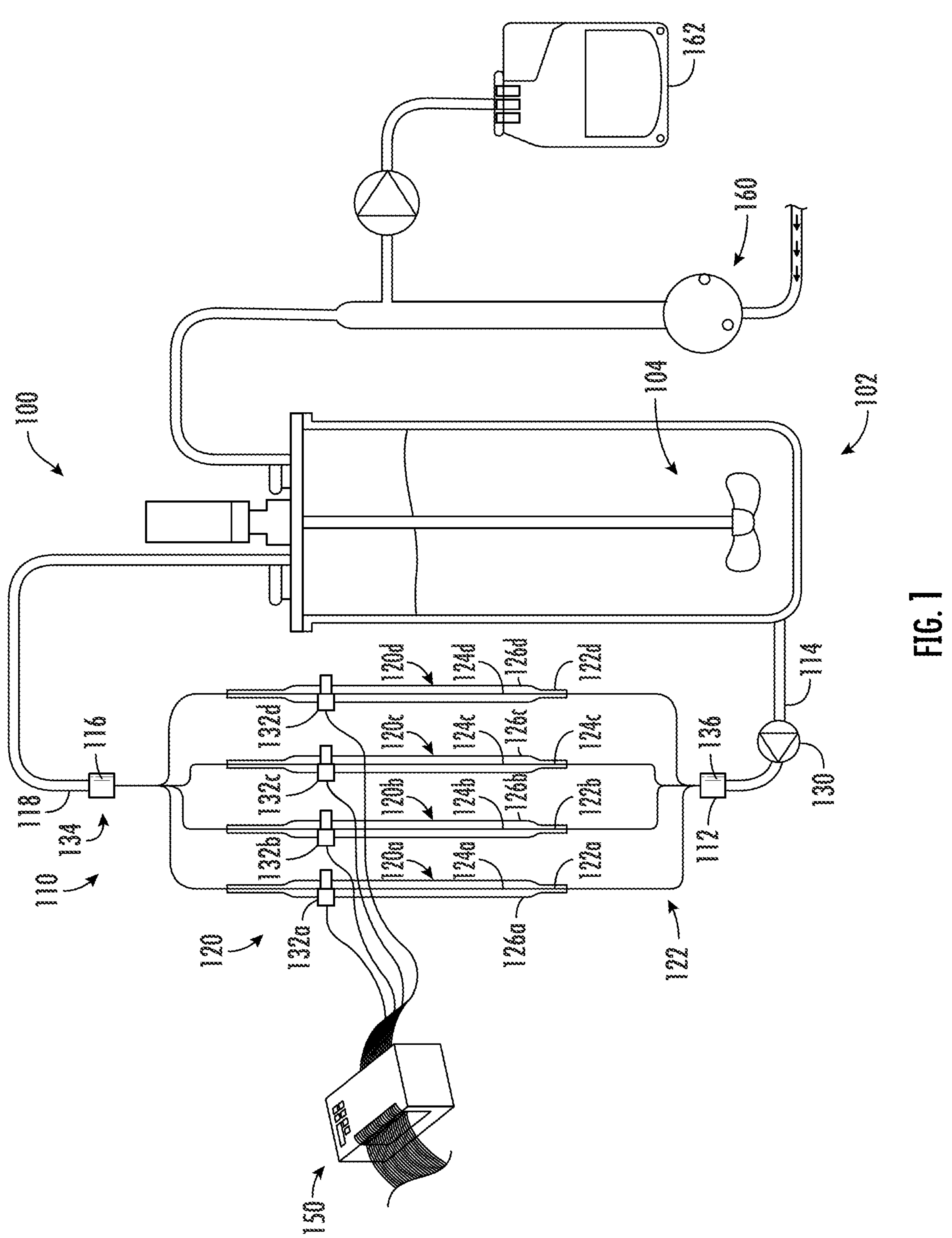
FIG. 1 illustrates a schematic view of a screening system in accordance with various aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

Features, integers, characteristics, compounds, chemical moieties or groups described in conjunction with a particular aspect, embodiment, or example of the invention are to be understood to be applicable to any other aspect, embodiment, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The claimed invention is not restricted to the details of any foregoing embodiments. The claimed invention extends to any novel one, or any novel combination, of the features disclosed in this specification (including any accompanying claims, abstract and drawings), or to any novel one, or any novel combination, of the steps of any method or process so disclosed.

"Tangential flow filtration" or "TFF" or "crossflow filtration" refers to filtration processes in which the sample mixture circulates along the surface of the porous medium or membrane, while applied pressure causes certain solutes and small molecules to pass through the filter. Typically, the solution flows parallel or tangential to the filter medium or membrane (wall). A pressure differential across the membrane causes fluid and filterable solutes to flow through the filter. This can be conducted as a continuous-flow process, since the solution is passed repeatedly over the membrane while that fluid that passes through the filter is continually drawn off into a permeate stream. The materials to be collected are small enough (below the molecular weight cutoff or MWCO of the hollow fiber filters) to pass through the walls of the fiber filters with some liquid, which is collected as permeate. The permeate is isolated from the feed material and the retentate (remaining material which cannot pass through the membrane), and collected (generally as a cell-free harvest) in a collection or harvest vessel (e.g., a bag). The remaining fluid within the lumens of the hollow fiber filters is returned to the process vessel as retentate (generally a cell culture suspension).

Another processes, known as alternating tangential flow filtration (ATF), offers yet another mode of filtration. ATF is similar to TFF in that it generates a flow pattern parallel to the filtration membrane surface; however, it differs from TFF in that the direction of flow is repeatedly alternating or reversing across the filter surface. The alternating tangential flow filtration system includes consists of a filter element, commonly a hollow fiber cartridge, connected at one end to a reservoir containing the content to be filtered and at the other end connected to a diaphragm pump capable of receiving and reversibly expelling the unfiltered liquid flowing reversibly between reservoir and pump through the filter element. The system has shown the ability to sustain filtration of complex mixtures, including the medium of a cell culture, even when that medium is burdened with high cell concentration and other cellular products.

In accordance with various principles of the present disclosure, a screening tool, system, and method is provided to screen filter materials for use in filter modules, such as for hollow fiber filters used in hollow fiber filter modules. The present disclosure is configured to allow high throughput and fast processing rates, with high flux rates, to allow for testing of multiple chemistries and porosities and other properties of the hollow fibers. Typically, the properties of the membranes (i.e., the walls, such terms being used interchangeably herein without intent to limit) of the hollow fiber filters, may vary depending on the filter material from which the membrane is formed. The system may be modular and/or configurable for use in various processing systems. Various advantages of such tools, systems, and methods include smaller footprint, lower holdup, disposable flow paths, irradiatable flow paths, capability of being used upstream (e.g., in connection with a bioreactor or cell culture system/process) as well as downstream (e.g., in a process not involving a bioreactor), among other advantages.

In accordance with various principles of the present disclosure, the screening tool includes two or more separate filter modules, each filter module having a housing (which may also be referenced as a cartridge, such terms being usable interchangeably herein without intent to limit) containing one or more hollow fiber filters. The filter housings of the filter modules are preferably substantially identical, and may be formed of the same generally fluid-impermeable material capable of withstanding pressures generated during operation of the screening tool. The one or more hollow fiber filters extend generally longitudinally within the filter housing. The hollow fiber filters may be potted at each end of the filter housing with a potting material such as known in the art (e.g., epoxy or polyurethane), such as to be stabilized with respect to the filter housing.

In accordance with various further principles of the present disclosure, each filter module may house one or more hollow fiber filters of a filter material different from the filter material of the hollow fiber filters of the other filter modules. The different filter materials may vary in one or more properties, such as chemistry, porosity, morphology, geometry, configuration, modality, etc., which may affect the permeate filtered therethrough. A common feedstream may be fed to the screening tool and divided into separate flow paths. It will be appreciated that the term feedstream may be used interchangeably herein with terms such as feed material or feed stock without intent to limit, and the term flow path may be used interchangeably herein with flow stream or flow stream path without intent to limit. The feedstreams through each flow path are each fed under substantially identical conditions. As such, the individual filter modules are subjected to substantially the same conditions for filtration, other than the differences among the filter materials. The permeate exiting the hollow fiber filters in each filter module is isolated so that the performance of the hollow fiber filter materials used in each filter module may be assessed. For instance, rate (flux), efficiency, quality of permeate products (e.g., whether intact or otherwise affected by the filter material), flow pressures, shear rates/impact, permeability, and other filter performance factors may be assessed (such term being used interchangeably herein with terms such as measured, analyzed, determined, evaluated, tested, compared, screened, etc., and conjugations thereof, without intent to limit) among the filter modules. Such an arrangement provides real time performance assessments of different filter materials under substantially identical conditions, as the same feed material is passed through the different filter materials under substantially identical conditions, and the permeate passing through the different filter materials is evaluated at substantially the same time. For instance, the same feedstream may be fed into each filter module at the same flux or feed pressure. A common pump may be used to pump the feedstream through the filter modules. Generally, it is desirable to use a pump, such as a peristaltic or magnetic levitation pump, rather than relying on gravity, for controlled movement of the feedstream through the screening system. The feedstream may be sourced from a vessel (such term being used interchangeably herein with terms such as chamber, container, bag, etc., without intent to limit) containing the feed materials. The container from which the feedstream is fed to a screening tool in accordance with various principles of the present disclosure may be referenced herein as a process vessel, a feed vessel, a feed reservoir, etc., and such terms may be used interchangeably herein without intent to limit, reference generally being made to a process vessel for the sake of simplicity with without intent to limit. The process vessel may or may not perform a process on the feed materials therein. In some embodiments, the process vessel actively processes feed materials. For instance, the process vessel may be a bioreactor for growing cell cultures or other processing vessel configured to process a fluid to be fed through a screening tool formed in accordance with various principles of the present disclosure.

Once the feed material is driven into the screening tool (e.g., through a common inlet/feed port), the feed material preferably flows in parallel flow paths, each flow path passing through one of the multiple filter modules and hollow fiber filters. An additional pumping system (either a common multi-channel pump controlling each filter module individually, or a separate pump for each filter module) may be used to pull permeate material (fluid and particles below the MWCO of the hollow fiber filter material within the filter module) through the hollow fiber filter(s) within each module. Preferably, the channels of the common pump, or the multiple pumps, distribute force equally across the hollow fiber filters.

In accordance with various principles of the present disclosure, a sensor may be associated (e.g., coupled) with each filter module with a filter to be analyzed (e.g., compared with a different filter of another filter module). The sensor may sense, gather, indicate, and/or transmit various properties or characteristics, etc., of the filter material, such as by sensing, gathering, indicating, and/or transmitting various properties or characteristics, etc., of permeate flowing through the filter. It will be appreciated that references to any of sensing, gathering, indicating, and/or transmitting herein should be understood as including one or more than one or all such operations, unless otherwise indicated.

In some embodiments, each filter module or pump (or component of a multi-channel pump) includes a pressure sensor to monitor pressure through the filter module associated with (i.e., acted upon by) a given pump. In some embodiments, a separate sensor or transducer is provided to measure alternative or additional properties or characteristics of feed, permeate, and retentate flow for the hollow fiber filter(s) of each fiber filter module. Accordingly, the present disclosure provides a high throughput hollow fiber screening tool/device, system, and method for comparison and screening more than one type of filter material. Higher throughput may be achieved over prior devices sequentially analyzing filter modules with multiple fibers all of the same type, and not testing different fiber types under substantially identical conditions.

In accordance with an aspect of the present disclosure, a filter unit may include a manifold configured for mounting two or more filter modules to be screened by a screening tool. The manifold may be configured to facilitate parallel flow paths (e.g., by splitting or dividing the feedstream into a separate flow path for each filter module) through the filter unit, preferably each under substantially the same flow conditions. Feedstream in each flow path is directed into an associated one of the two or more filter module, each filter module being associated (in fluid communication with) a different one of the flow paths. The end of at least one (and generally both) of the filter modules may be potted into a respective endcap of the filter unit manifold. Additionally or alternatively, a connector, such as a TC (triclamp) fitting, or a luer connector (e.g., as a female luer connector) may be provided on one or both ends of at least one of the filter modules to facilitate coupling to an endcap of the manifold, such as by coupling with a corresponding connector (mating, or otherwise configured to be coupled with a connector on the filter module). Use of connectors may facilitate subsequent removal of the filter module from the filter unit and/or rapid exchange with another filter module with the same or different properties (e.g., the same or different filter elements therein). Such connections facilitate simple and quick setup of the screening system, and the ability to change out filter units for different experiments.

In accordance with an aspect of the present disclosure, each filter module may be formed of significantly fewer fibers than used in prior art filter modules. For instance, fewer than 20 fibers are used, such as fewer than 15, or fewer than 10, and as few as 1-5 fibers (including increments of 1 fiber from 1 to 20 fibers). As such, in contrast with a typical filter module containing on the order of 10,000 individual fibers, a filter module formed in accordance with various principles of the present disclosure has significantly fewer fibers, and may be processed in parallel with other filter modules without detracting from the speed and efficiency of the filtration process. A screening tool and system formed in accordance with various principles of the present disclosure may be used in small scale testing, such as testing of approximately 2 liters of fluid at a time. Filtering through multiple such filter modules does not significantly impact the throughput speed or efficiency of the filter unit.

Because the flow of feed materials through each filter module is substantially uniform, pressure differences measured across the filter modules in the filter unit will be filter membrane material dependent, such as based on how the feed material (e.g., cell culture) interacts with the fiber material itself. The variability of differences in the flow of feed material (e.g., from different bioreactors, or different batches, or different points in time in the development of a particular batch, or differences in other environmental factors, etc.) common to prior screening tools and systems is thus essentially eliminated.

The present disclosure provides a method of screening which includes comparing throughput of each of two or more fiber filter modules to evaluate performance and other properties or characteristics of the materials of the different fibers thereof. The method facilitates high throughput consistent testing across different fiber materials, such as with different properties and/or sources (e.g., manufacturers). If desired, in addition to testing conditions in situ within various hollow fiber filters, the permeate collected from filter modules may also be tested or analyzed, and compared with permeate collected from other filter modules. For instance, the quality or nature of the product of interest (such as antibodies, particularly monoclonal antibodies, other proteins, viruses, and/or other cellular matter) in the permeate which flows through the hollow fiber filter membranes of the various filter modules may be analyzed and compared.

Embodiments of screening tools and systems, and associated methods, will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, common features are identified by common reference elements and, for the sake of brevity, the descriptions of the common features are generally not repeated. Certain features in one embodiment may be used across different embodiments and are not necessarily individually labeled when appearing in different embodiments. For purposes of clarity, not all components having the same reference number are numbered. Moreover, a group of similar elements may be indicated by a number and letter, and reference may be made generally to one or such elements or such elements as a group by the number alone (without including the letters associated with each similar element).

With reference to FIG. 1, a screening system 100 for use in a tangential flow filtration (TFF) system is illustrated schematically. A screening tool 110 is shown in a flow path of a system (e.g., a filtration system) providing a feedstream of feed material to be screened by the screening tool 110.

More particularly, the screening tool 110 is illustrated in fluid communication with an example of a process vessel 102 containing feed material 104 to be passed (such as with the assistance of a feed pump 130) into a screening tool inlet 112 (e.g., a feed port) of the screening tool 110 via a feedline 114. The feed material 104 is fed (e.g., driven, such as pumped) into hollow fiber filter modules 120 of the screening tool 110 through a filter module inlet 122, and through the different hollow fiber filters 124 (within the filter modules 120) to be screened by the screening tool 110. In the illustrated example, the feed material 104 passes through the screening tool 110, exits via the screening tool outlet 116, and is returned to the process vessel 102 via a retentate line 118. However, other configurations, such as passing of permeate to a collection vessel, are within the scope of the present disclosure.

In accordance with various principles of the present disclosure, the screening tool 110 has a plurality of filter modules 120*a*, 120*b*, 120*c*, 120*d* (referenced generally with reference numeral 120), and may be considered a testing manifold composed of multiple filters. Although four (4) separate filter modules 120*a*, 120*b*, 120*c*, 120*d* are illustrated, it will be appreciated that two or more, such as three, five, or more than five, filter modules may be provided. Each of the filter modules 120*a*, 120*b*, 120*c*, 120*d* has a separate filter housing 126*a*, 126*b*, 126*c*, 126*d* configured to contain at least one respective hollow fiber filter 124*a*, 124*b*, 124*c*, 124*d* to be screened by the screening tool 110. The separate filter housings 126*a*, 126*b*, 126*c*, 126*d* fluidly isolate the respective different types of hollow fiber filters 124*a*, 124*b*, 124*c*, 124*d* to be evaluated and compared with the use of the screening tool 110 so that permeate through a given hollow fiber filter 124 of a given filter module 120 may be individually screened separately from permeate through other hollow fiber filters 124 of other filter modules 120. The filter housings 126*a*, 126*b*, 126*c*, 126*d* may be made of a flexible material, such as polysulfone, which can encase the respective hollow fiber filters 124*a*, 124*b*, 124*c*, 124*d* to provide sufficient rigidity to the fibers so that the feed material passes through the hollow fiber filters in a substantially linear manner, as well as to contain permeate therein.

In accordance with an aspect of the present disclosure, the screening tool 110 is configured to screen more than one type of hollow fiber filter. The hollow fiber filters 124*a*, 124*b*, 124*c*, 124*d* can be made of various different formulations of materials, such as polysulfone, or polyether sulfone or polyvinylidene fluoride (PVDF). The material from which the hollow fiber filters 124*a*, 124*b*, 124*c*, 124*d* may be formed can have at least one variable (e.g., different property, material, manufacturer, etc.) to be compared. As such, the one or more hollow fiber filters of each filter module 120*a*, 120*b*, 120*c*, 120*d* are different from the one or more hollow fiber filters 124 of the other filter modules 120 of the screening tool 110. In other words, each of the filter modules 120*a*, 120*b*, 120*c*, 120*d* can contain different type of hollow fiber filter 124*a*, 124*b*, 124*c*, 124*d*, made of hollow fiber filter material that is different from the hollow fiber filter 124 in any of the other filter modules 120*a*, 120*b*, 120*c*, 120*d*. In order to accurately compare the material properties or characteristics of interest (e.g., performance, efficiency, rate or flux, etc.), the dimensions (inner diameter and outer diameter, and thus membrane thickness, as well as length) of the hollow fiber filters 124 of the various filter modules 120 of the screening tool 110 are substantially the same. Moreover, to achieve an accurate comparison, the feed material 104 is fed into the filter modules 120*a*, 120*b*, 120*c*, 120*d* in substantially parallel flow paths at substantially the same rate, via a single feed stream 114 provided via pump 130. Preferably, the distance from the screening tool inlet 112 to each of the filter module inlets 122*a*, 122*b*, 122*c*, 122*d* is substantially equal (as described in further detail below). By providing substantially the same conditions for filtration through each filter module 120, the materials of the hollow fiber filters 124*a*, 124*b*, 124*c*, 124*d* of each of the various filter modules 120*a*, 120*b*, 120*c*, 120*d* may be accurately compared for screening purposes, such as to select the appropriate hollow fiber filter 124 for a particular purpose (e.g., to harvest particular permeate materials of interest).

In accordance with another aspect of the present disclosure, the screening tool 110 is configured for screening purposes and as a small scale high throughput hollow fiber filter system. Accordingly, for such purposes, the filter modules 120 (at least one and preferably all of the filter modules 120) of the screening tool 110 contain no more than twenty (20) hollow fiber filters 124, and preferably fewer than fifteen (15), and preferably fewer than twelve (12), and, generally no more than ten (10) hollow fiber filters 124, and even as few as one (1) to three (3) hollow fiber filter 124, including increments of individual fibers therebetween. In one non-limiting example embodiment each hollow fiber may have an inner diameter of 0.5 mm. It will be appreciated that the maximum/minimum inner and outer diameters of the hollow fibers are generally dependent on the number of fibers/module, and/or the packing density. As such, a decrease in fiber outer diameter allows for an increase in the number of fibers which may be used. Generally, the length of each fiber is significantly larger than the diameter thereof, such as to facilitate handling of the fibers. For instance, the length of the fibers generally is at least about 20 cm and may be as long as about 60 cm (including increments of 0.5 cm therebetween), such as may be determined or dictated by typical filter housing lengths.

As noted above, feed material 104 from the process vessel 102 flows through an inlet 112 of the screening tool 110. Typically, feed material 104 is fed through the bottom of a filter unit. Accordingly, in the embodiment illustrated in FIG. 1, feed material 104 is fed into a screening tool inlet 112 at the bottom of the screening tool 110 to the bottom of vertically positioned filter modules 120 of the screening tool 110. The feed material 104 is driven, such as by a feed pump 130, upwardly through the screening tool 110. To screen different filter modules 120 (each containing at least one hollow fiber filter 124 with properties unique and different from the properties of hollow fiber filters 124 of another filter module 120), the feedstream 104 from the feed pump 130 is split substantially evenly into separate flow paths to flow through each of the filter modules 120*a*, 120*b*, 120*c*, 120*d* at substantially the same rate and flow volume. More particularly, a feedstream from a single feed line 114 is split into multiple filter module inlets 122*a*, 122*b*, 122*c*, 122*d* (one for each of the filter modules 120*a*, 120*b*, 120*c*, 120*d*) to feed into the different hollow fiber filter 124*a*, 124*b*, 124*c*, 124*d*. The distance from the screening tool inlet 112 to each of the filter module inlets 122*a*, 122*b*, 122*c*, 122*d* preferably is substantially equal to maintain similar flow conditions through each filter module 120*a*, 120*b*, 120*c*, 120*d*.

The feed material 104 is introduced into the inner lumen of the one or more hollow fiber filter 124*a*, 124*b*, 124*c*, 124*d* of each of the filter modules 120*a*, 120*b*, 120*c*, 120*d* respectively. Pump 130 can be a peristaltic, bidirectional, diaphragmatic, or pneumatic pump, and may be used to apply pressure to the feed material 104 to drive the feed material through the membranes of the hollow fiber filters 124. In the illustrated embodiment, a single pump 130 is provided for all of the filter modules 120*a*, 120*b*, 120*c*, 120*d*. The single pump 130 facilitates driving feedstreams through each filter module 120*a*, 120*b*, 120*c*, 120*d* at the same rate. As will be appreciated, this arrangement is effective for applications in which the hollow fiber filters 124*a*, 124*b*, 124*c*, 124*d* of each of the filter modules 120*a*, 120*b*, 120*c*, 120*d* all have the same inner diameter. Where all hollow fiber filters 124*a*, 124*b*, 124*c*, 124*d* have the same filter IDs, each of the hollow fiber filters 124*a*, 124*b*, 124*c*, 124*d* can differ from one or more of the other hollow fiber filters 124*a*, 124*b*, 124*c*, 124*d* by membrane material, pore size, permeability, membrane structure, wall thickness, and the like.

Each filter module 120*a*, 120*b*, 120*c*, 120*d* may have a separate permeate outlet 132*a*, 132*b*, 132*c*, 132*d* (illustrated in greater detail in FIG. 2) fluidly coupled to a permeate pump 150, which in the illustrated embodiment is a multi-channel permeate pump. In some embodiments the multi-channel permeate pump can be a peristaltic pump, a magnetic levitating pump, or other appropriate pump type. The permeate pump 150 may draw permeate from the outlets 132*a*, 132*b*, 132*c*, 132*d* and may return the withdrawn permeate to the process vessel 102.

To collect data for screening of the hollow fiber filters 124, one or more sensors (not shown) may be positioned at various locations within the system 100 to sense, gather, indicate, and/or transmit various properties or characteristics of the retentate and/or the permeate which has passed through the membranes of the hollow fiber filters 124*a*, 124*b*, 124*c*, 124*d* and has collected within the extra-capillary space of the housings 126*a*, 126*b*, 126*c*, 126*c*. In some embodiments a feed pressure can be monitored using a sensor positioned in the feedline 114 downstream of the feed pump 130 and upstream of the hollow fiber filters 124*a*, 124*b*, 124*c*, 124*d*. Individual sensors can be positioned upstream of each of the hollow fiber filters 124*a*, 124*b*, 124*c*, 124*d* to sense individual feed pressures, or a sensor can be disposed in the common feedline 114 to sense common feed pressure. In some embodiments retentate pressure can be monitored using a sensor positioned in the retentate line 118 downstream of the hollow fiber filters 124*a*, 124*b*, 124*c*, 124*d*. Individual sensors can be positioned downstream of each of the hollow fiber filters 124*a*, 124*b*, 124*c*, 124*d* to sense individual retentate pressures, or a sensor can be disposed in the common retentate line 118 to sense common retentate pressure. In some embodiments permeate pressure can be monitored using sensors positioned between the permeate outlets 132*a*, 132*b*, 132*c*, 132*d* of the hollow fiber filters 124*a*, 124*b*, 124*c*, 124*d* and the permeate pump 150. Various properties or characteristics of the material of the hollow fiber filters 124*a*, 124*b*, 124*c*, 124*d* may thereby be assessed. Filter module sensors typically are pressure sensors (e.g., pressure transducers), but may be any other type of desired sensor (or multi-modal sensor) for detecting, gathering, indicating and/or transmitting the desired data of interest (e.g., pressure, flow rate, etc.) It will be appreciated that a screening tool 110 formed in accordance with various principles of the present disclosure can include any of a variety of sensors other than pressure sensors, such as conductivity sensors, temperature sensors, flow sensors, ultraviolet or UV sensors, turbidity sensors, and/or combinations thereof. At least one system controller (such as in the form of a programmable logic controller containing a plurality of proportional-integral-derivative controllers) can be coupled to the sensors to provide desired analysis and information of interest. In one non-limiting example embodiment, the sensors can be used to determine and monitor protein passage rate through each of the hollow fiber filters 124*a*, 124*b*, 124*c*, 124*d*. The protein passage rate and pressure profiles indicate the performance of the filter modules 120*a*, 120*b*, 120*c*, 120*d*. Similar data can be generated and compared for each filter module 120*a*, 120*b*, 120*c*, 120*d* in the screening tool 110.

Figure 2:
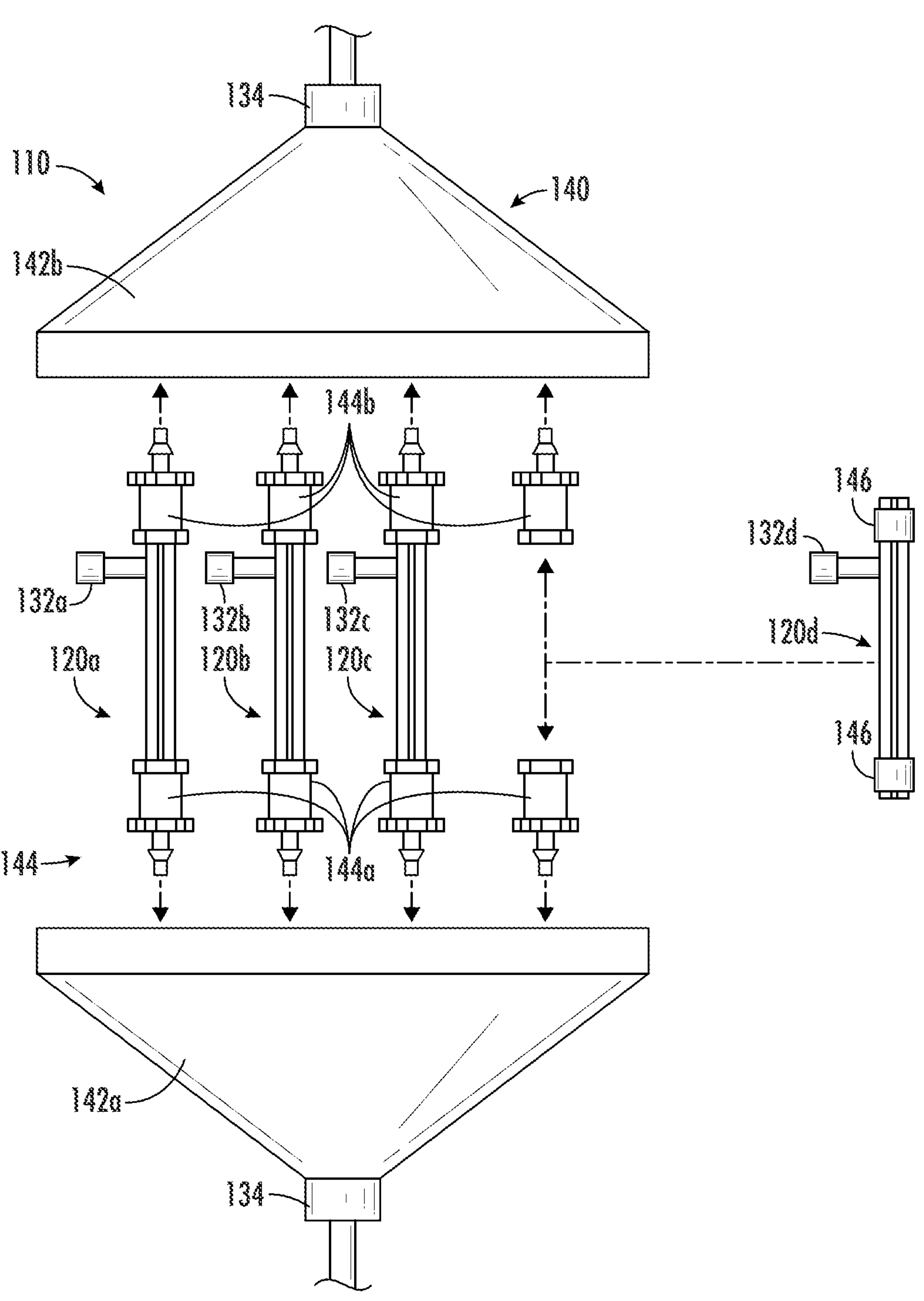
FIG. 2 illustrates a schematic and partially exploded view of a portion of the screening system of FIG. 1.

In accordance with various principles of the present disclosure, and as illustrated in FIG. 2, the screening tool 110 may include a manifold 140 configured to hold or support the various filter modules 120*a*, 120*b*, 120*c*, 120*d* of the screening tool 110. The manifold 140 may be configured with multiple flow paths therein to introduce substantially the same flow of feed material 104 into the filter modules 120*a*, 120*b*, 120*c*, 120*d* of the screening tool 110 to compare the properties of the different hollow fiber filter 124*a*, 124*b*, 124*c*, 124*d* among the filter modules 120*a*, 120*b*, 120*c*, 120*d*.

The non-limiting example of an embodiment of a screening tool manifold 140 illustrated in FIG. 2 has endcaps 142*a*, 142*b* each in the form of a cone, although other shapes are within the scope of the present disclosure. The filter modules 120*a*, 120*b*, 120*c*, 120*d* are illustrated in an exploded position away from the endcaps 142*a*, 142*b* to illustrate manifold fittings 144*a*, 144*b* associated with each end cap 142*a*, 142*b* and to which the filter modules 120*a*, 120*b*, 120*c*, 120*d* are coupled. The manifold fittings 144*a*, 144*b* may be luer or triclamp (TC) fittings, or other suitable fittings allowing coupling with a fitting 146 (shown on filter module 120*d*, uncoupled from respective manifold fittings 144*a*, 144*b*) on a respective filter module 120*a*, 120*b*, 120*c*, 120*d*. It will be appreciated that although four filter modules 120*a*, 120*b*, 120*c*, 120*d* and four pairs each of associated manifold fittings 144*a*, 144*b* are illustrated, as few as two or three, or more than four filter modules and associated manifold fittings may be provided. Additionally or alternatively, potting materials may be used to hold each filter module 120 in place with respect to the end caps 142*a*, 142*b* of the manifold 140. Any type of potting compound known or heretofore known in the art, such as 1-component, 2-component, or 3-component adhesives (for example, epoxy resin, polyurethane), thermoplastic materials (for example, polyethylene hotmelts) or reactive thermoplastic materials (for example, thermally processable polyurethane), or other curable liquid compounds (for example, liquid ceramic) or other polymers such as polyurethane resin, silicon resin, epoxy resin, can be used for each filter module 120.

The manifold fittings 144 may be configured to direct or distribute the feedstream substantially equally into each of the filter modules 120*a*, 120*b*, 120*c*, 120*d* to be screened. Each manifold fitting 144 of the screening tool 110 may be configured to mate with a corresponding filter module fitting 146 on an end of a respective filter module 120 to be mounted therewith. For instance, a male luer fitting may be provided on at least one end of a filter module 120, and a rotating female locking ring may be provided in the endcap 142*a*, 142*b* of the filter unit, the male luer fitting locking with the rotating ring of the female luer fitting. A reverse configuration is within the scope of the present disclosure as well. In some embodiments, the fittings are distributed substantially equidistantly (e.g., radially outward at the same distance) from the screening tool inlet 112 (FIG. 1) to maintain substantially the same feed conditions for the feed material 104 flowing into each filter module. It will be appreciated that manifold fittings 144*b* similar to manifold fittings 144*a* illustrated in bottom end cap 142*a* may be provided in top end cap 142*a* of manifold 140, as illustrated in FIG. 2. Such elements are similar to or substantially the same as the above-described elements associated with the bottom end cap 142*a* and thus description thereof is not repeated for the sake of simplicity and brevity. Similarly, a filter module fitting 146 may be provided on either or both ends (bottom/top) of one or more of the filter modules 120*a*, 120*b*, 120*c*, 120*d* to be mounted in the manifold 140.

Returning to the screening system 100 illustrated in FIG. 1, data from the various filter module sensors is analyzed by a sensor controller or other controller or processor or computer capable of gathering and analyzing the data of interest, such as a pump system/computer. The desired analyses, comparisons, etc. of the hollow fiber filters 124*a*, 124*b*, 124*c*, (e.g., filter performance analysis, such as of product sieving and permeate pressure) are performed in an appropriate manner as known or heretofore known to those of ordinary skill in the art, the present disclosure not being limited by a particular mode of analysis or otherwise.

It will be appreciated that a feed sensor 136 may be provided at the screening tool inlet 112 to sense desired data (e.g., pressure, flow rate, etc.) in connection with the feed material 104 flowing into the screening tool 110. Similarly, a retentate sensor 134 may be provided at the screening tool outlet 116 to sense desired data (e.g., pressure, flow rate, etc.) in connection with the retentate/feed material 104 flowing out of the screening tool 110. Such sensors and associated equipment for analyzing the sensed data are known in the industry and details thereof are not critical to the present disclosure and thus not provided herein for the sake of brevity.

The example illustrated in FIG. 1 is illustrated for upstream use in connection with, for instance, a process vessel 102 in the form of a bioreactor. In such example, in which the screening tool 110 may be used for screening purposes, the permeate flow path for each filter module 120 of the screening tool 110 is recirculated back into the bioreactor. Optionally, an ATF system 160 may be provided in fluid connection with the process vessel 102 to grow the cells for the feed material 104 or solution to be run through the screening tool 110 and to maintain a steady-state volume in the process vessel 102. The filter module for the ATF system 160 generally has many more fiber filters than any of the filter modules 120 of the screening tool 110. Feed material 104 from the process vessel 102 may be fed cyclically through the ATF system 160, with retentate (fluid containing cells) cycling back and forth between the process vessel 102 and the screening tool 110, while materials of interest (which are below the MWCO of the filter module of the ATF system 160) pass through the filter walls thereof as permeate. A permeate collection vessel 162 may be provided to collect waste products of the feed material 104.

Figure 3:
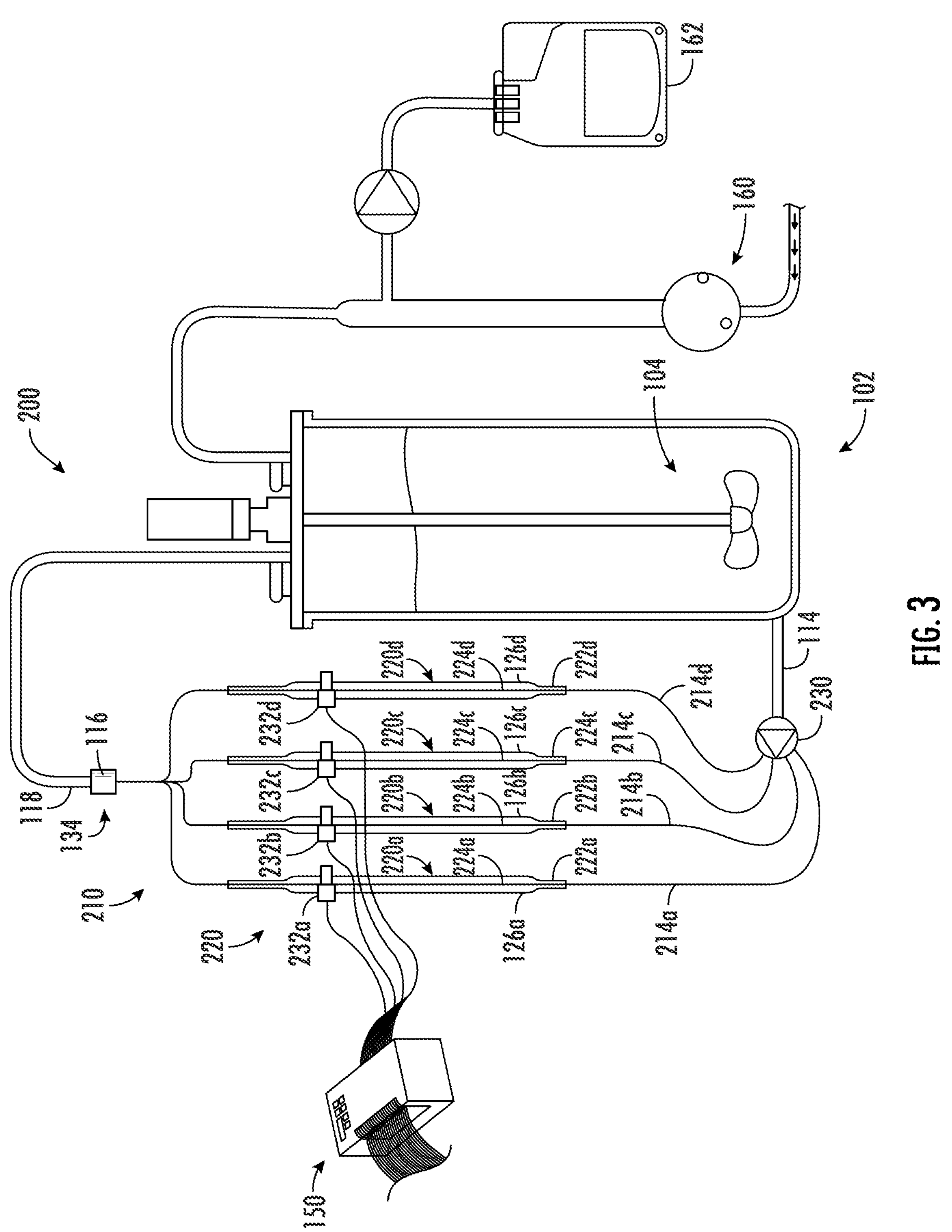
FIG. 3 illustrates a schematic view of a screening system in accordance with various aspects of the present disclosure.
Figure 4:
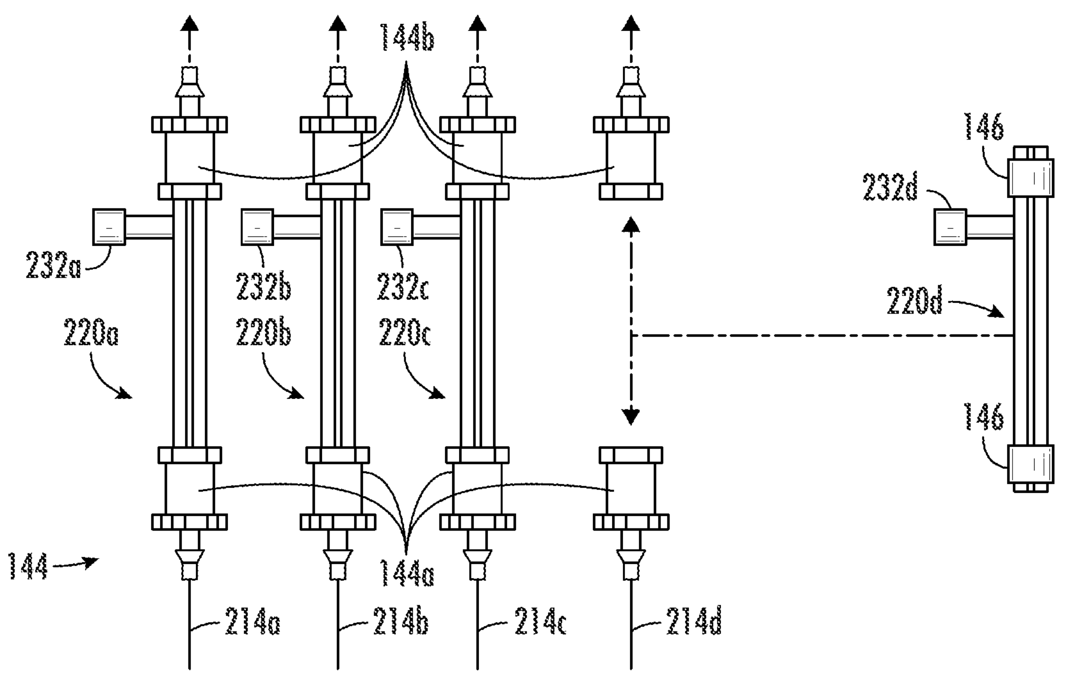
FIG. 4 illustrates a schematic and partially exploded view of a portion of the screening system of FIG. 3.
Figure 5:
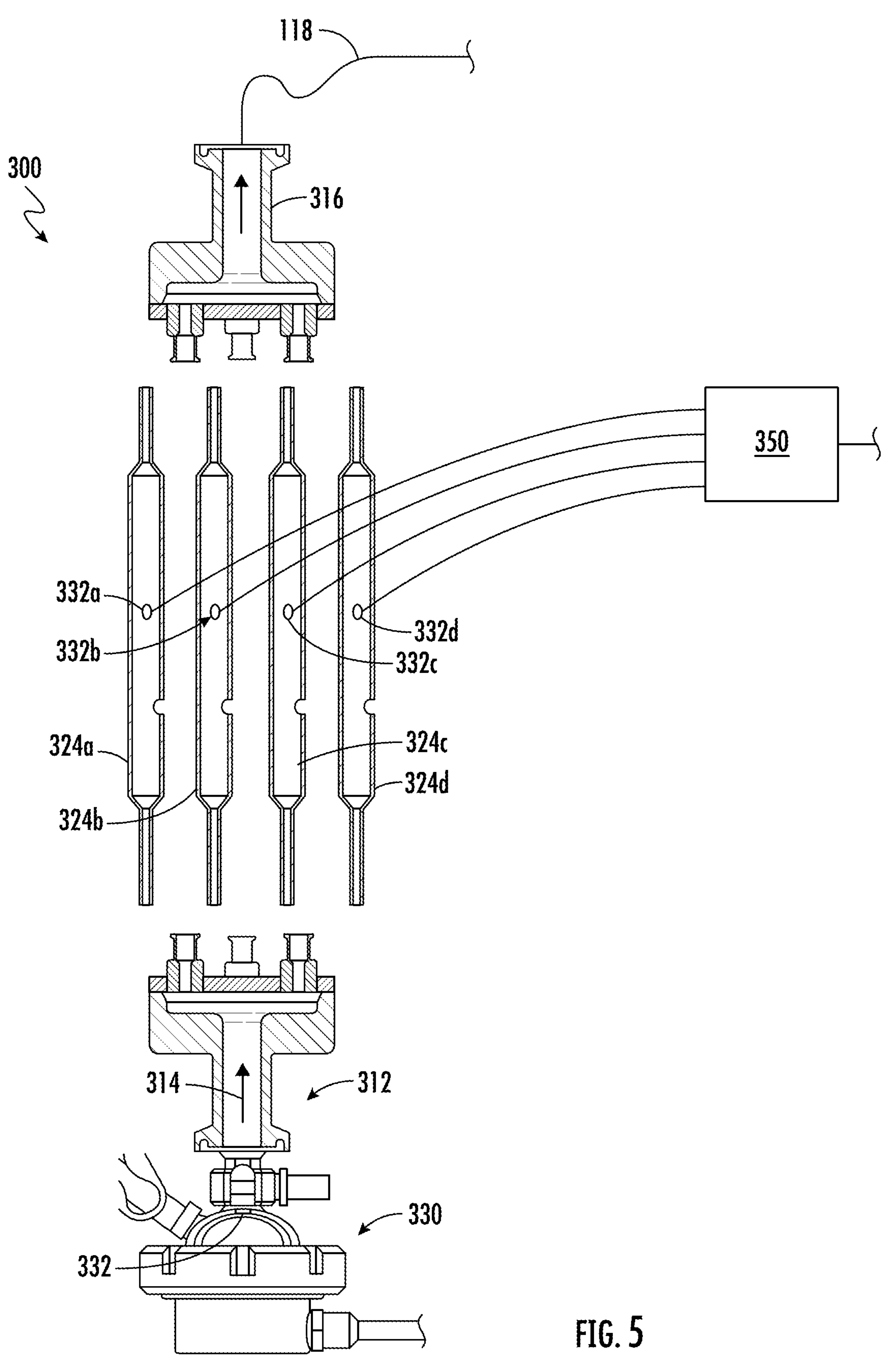
FIG. 5 illustrates a schematic and partially exploded view of a portion of a screening system in accordance with various aspects of the present disclosure.

Referring now to FIGS. 3 and 4, a screening system 200 for use in screening hollow fiber filters 224*a*, 224*b*, 224*c*, 224*d* for use in a tangential flow filtration (TFF) system will be described in greater detail. The screening system 200 is similar to the system 100 described in relation to FIGS. 1 and 2, with the exception that screening tool 210 includes a multi-channel feed pump 230 that takes feed material 104 from the process vessel 102 and provides individual flows of material 214*a*, 214*b*, 214*c*, 214*d* directly to each of the hollow fiber filters 224*a*, 224*b*, 224*c*, 224*d*. In one preferred example embodiment, the feed material 104 passes through the screening tool 210, exits via the screening tool outlet

216, and is returned to the process vessel 102 via a common retentate line 118. It will be appreciated that in some embodiments individual outlets (i.e., individual retentate lines from the individual hollow fiber filters 224*a*, 224*b*, 224*c*, 224*d*) can be fed back to the process vessel 102 through separate lines.

By providing a multi-channel pump 230 with a separate channel associated with each filter module 220*a*, 220*b*, 220*c*, 220*d*, the same flow rate can be provided through each filter module 220*a*, 220*b*, 220*c*, 220*d* regardless of the dimensions (e.g., inner diameter) of each of the hollow fiber filters 224*a*, 224*b*, 224*c*, 224*d* contained therein. Thus, the screening system 200 provides an increased versatility in simultaneous testing of a variety of hollow fiber filters.

In some embodiments, a separate pump can be used for each of the separate filter modules 220*a*, 220*b*, 220*c*, 220*d*. As will be appreciated, the screening system 200 can be used for simultaneous testing of multiple hollow fiber filters 224*a*, 224*b*, 224*c*, 224*d* having different hollow fiber materials, pore sizes, wall thicknesses, and/or having different dimensions (e.g., inner diameters (ID)).

Similar to the prior embodiment, the multichannel recirculation pump 230 takes suction from the process vessel 102, and separately drives feed flow 214*a*, 214*b*, 214*c*, 214*d* to each of the inlets 222*a*, 222*b*, 222*c*, 222*d* of each of the individual filter housings 220*a*, 220*b*, 220*c*, 220*d*. Permeate ports 232*a*, 232*b*, 232*c*, 232*d* associated with each of the separate filter modules 220*a*, 220*b*, 220*c*, 220*d* are fluidly coupled to permeate pump 150, which in the illustrated embodiment is a multichannel permeate pump. The permeate pump 150 can draw permeate from the outlets 232*a*, 232*b*, 232*c*, 232*d* and can return the withdrawn permeate to the process vessel 102.

Sensors (not shown) similar to or the same as those described in relation to the embodiment of FIGS. 1 and 2 can be associated with each filter module 220*a*, 220*b*, 220*c*, 220*d* and can be coupled to a controller (not shown) to collect desired information about the performance of each hollow fiber filters 224*a*, 224*b*, 224*c*, 224*d*.

As mentioned, by providing separate feed streams 214 to each of the individual hollow fiber filters 224*a*, 224*b*, 224*c*, 224*d* allows multiple different filter types and sizes (e.g., different inner diameters) in a single system. The system 200 of FIGS. 3 and 4 could also be used to test a variety of different feed streams against hollow fiber filters 224*a*, 224*b*, 224*c*, 224*d* having the same filter type and/or size.

Except as noted above, all other operational and structural aspects of the embodiment of FIGS. 3 and 4 are the same or similar to those described in relation to FIGS. 1 and 2, and thus will not be repeated.

FIGS. 5 and 6A-6C illustrate a further embodiment of a screening system 300 for use in screening hollow fiber filters 324*a*, 324*b*, 324*c*, 324*d* for use in alternating tangential flow (ATF) systems. Although the illustrated embodiment does not expressly illustrate the individual filter housings, permeate pump, process vessel, or other aspects of the screening system 300, it will be appreciated that those elements are included in the present embodiment. For the sake of brevity their description is not included.

The screening system 300 may be arranged and configured to allow for screening of hollow fiber filters 324*a*, 324*b*, 324*c*, 324*d* in much the same manner as described in relation to the previous embodiments. Thus, a feed pump 330 may operate to pass feed flow through a plurality of hollow fiber filters 324*a*, 324*b*, 324*c*, 324*d* having different characteristics (e.g., different material types, different pore sizes, different permeability, different membrane structure, different wall thickness, and the like).

The feed pump 330 may be fluidly coupled to a screening tool inlet 312, which can be configured to direct feed flow 314 through the plurality of hollow fiber filters 324*a*, 324*b*, 324*c*, 324*d*. A screening tool outlet 316 may be positioned to receive a retentate 118 flow from the plurality of hollow fiber filters 324*a*, 324*b*, 324*c*, 324*d* and to direct that flow to a process vessel (not shown). In the present embodiment, the pump 330 may be an ATF pump having a diaphragm 332 configured to move in a cyclic fashion to direct flow back and forth through the plurality of hollow fiber filters 324*a*, 324*b*, 324*c*, 324*d*. A plurality of separate permeate outlets 332*a*, 332*b*, 332*c*, 332*d* associated with the respective hollow fiber filters 324*a*, 324*b*, 324*c*, 324*d* are fluidly coupled to a permeate pump 350, which in the illustrated embodiment is a multichannel permeate pump. In some embodiments the multichannel permeate pump can be a peristaltic pump, a magnetic levitating pump, or other appropriate pump type. The permeate pump 350 draws permeate from the outlets 332*a*, 332*b*, 332*c*, 332*d* and may return the withdrawn permeate to the process vessel (not shown).

Sensors (not shown) similar to or the same as those described in relation to the embodiment of FIGS. 1 and 2 can be associated with each hollow fiber filters 324*a*, 324*b*, 324*c*, 324*d* and can be coupled to a controller (not shown) to collect desired information about the performance of each hollow fiber filter hollow fiber filter 324*a*, 324*b*, 324*c*, 324*d*.

By employing a feed pump 330 that includes an ATF hemisphere with a plurality of ports, flow can be distributed to the plurality of hollow fiber filters 324*a*, 324*b*, 324*c*, 324*d* having, for example, the same inner diameter and the same number of fibers so that testing of the different filter elements can be performed in ATF mode simultaneously. Such an arrangement allows simultaneous testing of the same or different filter elements so that data can be collected to characterize changes cause by different pore size, filter media types, and the like.

Figure 6A:
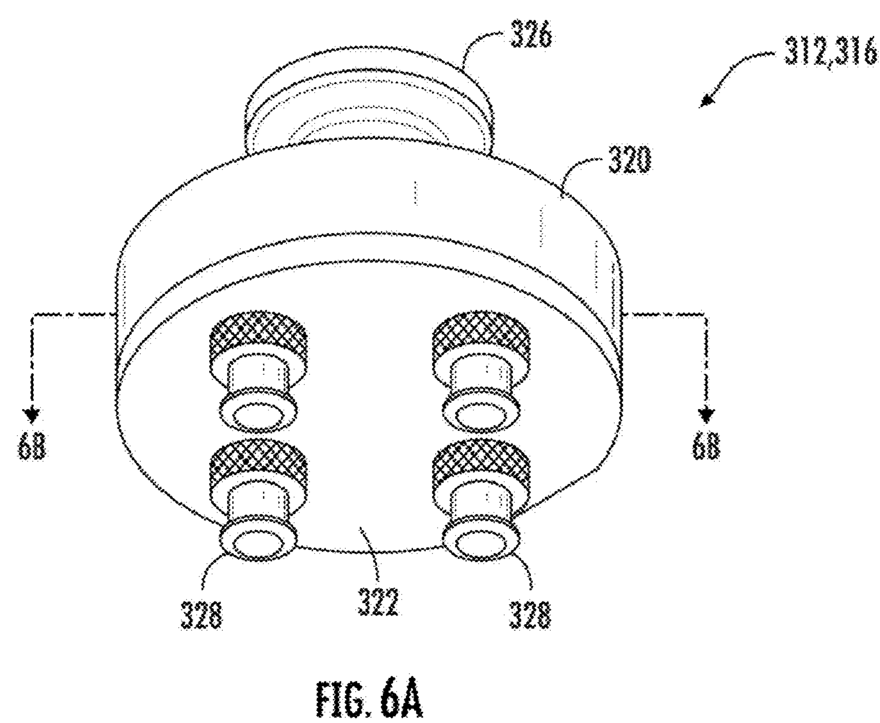
FIGS. 6A-6C are isometric, cross-section, and exploded views, respectively, of a portion of the screening system of FIG. 5.
Figure 6B:
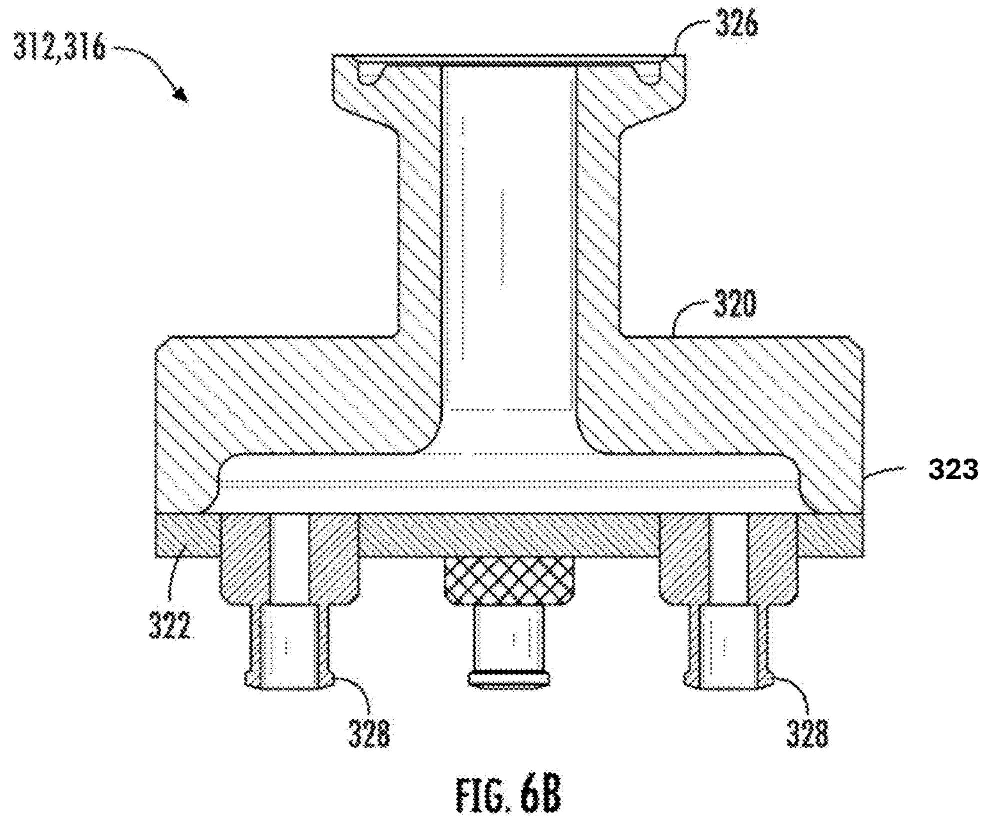
Figure 6C:
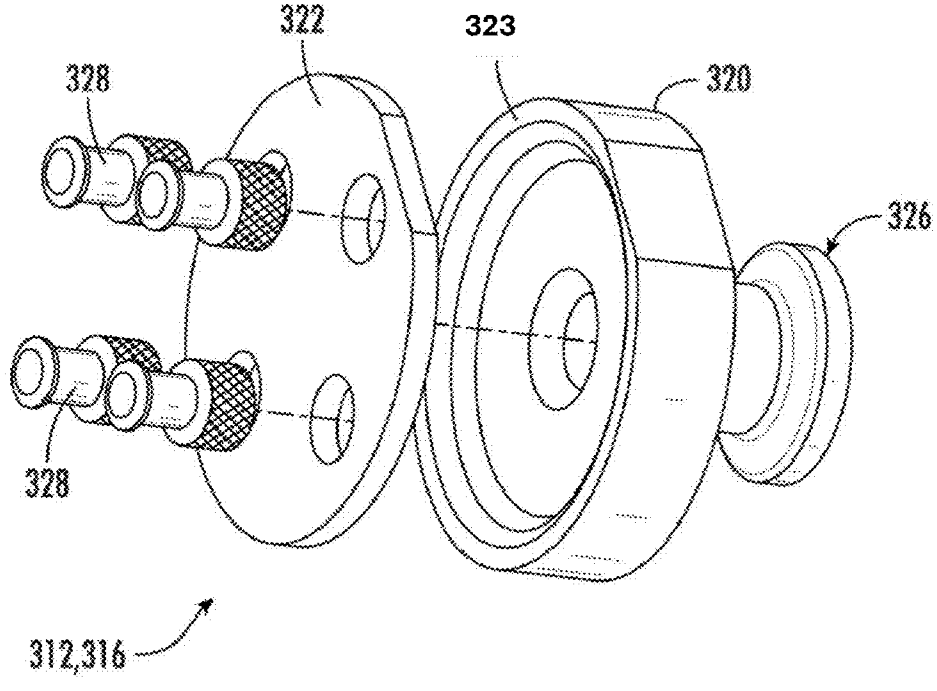

FIGS. 6A-6C illustrate an example fitting that can be used as a screening tool inlet 312 and/or screening tool outlet 316. The screening tool inlet/outlet 312, 316 can include a reducer portion 320 and a plate portion 322. The reducer portion 320 can have a first end 323 that is configured to receive the plate portion 322, and a second end 326 configured to couple to the feed line 314 or the retentate line 318. The plate portion 322 includes a plurality of fittings 328 each configured to engage a housing surrounding one of the hollow fiber filters 324*a*, 324*b*, 324*c*, 324*d* to be tested. The illustrated plate portion 322 is configured with four fittings 328, but it will be appreciated that greater or fewer fittings can be used. It will also be appreciated that multiple different plate portions 322, employing different numbers of fittings 328 can be interchanged with a single reducer portion 320.

The reducer portion 320 can be coupled to the plate portion 322 using any of a variety of connection techniques, including but not limited to welding, mechanical fasters, and the like. The second end 326 of the reducer portion 320 can be configured to couple to the feed line 314 or retentate line 318 via any known tube coupling arrangement. The fittings 328 can be configured to couple to the individual housings of the hollow fiber filters 324*a*, 324*b*, 324*c*, 324*d* in any of the manners described above in relation to the other embodiments disclosed herein.

In accordance with various principles of the present disclosure, methods of screening hollow fiber filters include comparing throughput of different hollow fiber filters to evaluate, determine, assess performance of the materials of the fibers thereof. The hollow fiber filters may be housed in hollow fiber filter modules, each filter module housing a hollow fiber filter with a different property or characteristic. The methods may further include use of a screening tool in which more than one filter module is provided, each filter module housing a hollow fiber filter with a unique property or characteristic. Medium may be passed or driven through the screening tool and various properties or characteristics of the hollow fiber filter may be assessed by evaluating different properties or characteristics of the feedstream, such as properties or characteristics of the permeate flowing through the hollow fiber filters.

Because different filters may be desired for different systems, a screening tool and system formed in accordance with various principles of the present disclosure, such as described above, allows relative simple and quick evaluation of two or more filters for selection of the best-suited filter type for a given process. Various principles of the present disclosure accordingly reduce the current struggle to identify the right filter types for a particular process.

It will be appreciated that principles of the present disclosure may be applied on a small scale for ready application to large-scale operations. Moreover, although the present disclosure is disclosed mainly with respect to small scale filtration systems (e.g., perfusion filter systems), the principles of the present disclosure may be applied to larger scale modules and/or systems.

It will further be appreciated that principles of the present disclosure may be applied beyond screening of different filter materials. For instance, a screening tool or system formed in accordance with various principles of the present disclosure allows for quick change out of filter modules, and thus may advantageously be used to shorten production time if replacement of clogged or fouled filters is required during production. Additionally or alternatively, if different permeate is desired from the same feedstream, or if separate tests are to be performed on different permeate flow paths, a screening unit such as disclosed herein may be advantageously used for such purposes, such as with a different hollow fiber filter in each of the different filter modules. The filters can be sized depending on the intended use of the tool and/or system. Advantageously, hollow fiber filter modules formed in accordance with principles of the present disclosure can be employed for different applications, for example, filtration, dialysis, osmosis, including reverse osmosis, separation, concentration of liquids, harvesting of cells, substances, antibodies or proteins, catalytic reaction of substances, adsorption or desorption of substances, enhancement of back filtration processes, gassing or degassing of media, physical transfer of heat, measurement of different parameters, such as pH value, temperatures, or the combination of two or several applications.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

Various structures and features of the embodiments described herein and illustrated in the figures have several separate and independent unique benefits. Therefore, the various structures and features described herein need not all be present in order to achieve at least some of the desired characteristics and/or benefits described herein. Moreover, the various features described herein may be used singly or in any combination. It will be appreciated that various features described with respect to one embodiment may be applied to another embodiment, whether or not explicitly indicated. Thus, it should be understood that one or more of the features described with reference to one embodiment can be combined with one or more of the features of any of the other embodiments described herein. That is, any of the features described herein can be mixed and matched to create hybrid designs, and such hybrid designs are within the scope of the present disclosure. Therefore, the present invention is not limited to only the embodiments specifically described herein. The above descriptions are of illustrative examples of embodiments only, and are not intended as limiting the broader aspects of the present disclosure.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A screening tool for screening a plurality of different filters, said screening tool comprising:

a plurality of filter modules, each of said plurality of filter modules having an inlet, an outlet, and a permeate disposed between the inlet and the outlet, the plurality of filter modules each further including a hollow fiber filter having a characteristic that is different from a characteristic of a hollow fiber filter of another one of the plurality of filter modules;

a screening tool inlet comprising a single inlet for receiving fluid therethrough, and a reducer portion, the reducer portion including a plate portion having a plurality of fittings coupled thereto, each of said plurality of fittings configured to directly engage the inlet of a separate one of said plurality of filter modules such that feed material flows directly from said single inlet to a respective inlet of each of the plurality of filter modules in parallel flow paths.

2. The screening tool of claim 1, wherein each filter module has fewer than ten hollow fiber filters, the hollow fiber filters of each filter module differing from the hollow fiber filters of another filter module of said screening tool.

3. The screening tool of claim 2, wherein each filter module has no more than three hollow fiber filters.

4. The screening tool of claim 1, further comprising at least one sensor associated with each filter module, said at least one sensor is selected from the group consisting of: a pressure sensor, a conductivity sensor, a temperature sensor, a flow sensor, an ultraviolet sensor, a turbidity sensor, or a combination thereof.

5. The screening tool of claim 1, wherein the inlet is configured to be coupled to an outlet of a pump so that a common flow of feed material is provided to each of the plurality of filter modules.

6. The screening tool of claim 5, wherein said screening tool further comprises a common outlet coupled to a process vessel.

7. The screening tool of claim 5, wherein the pump is an alternating tangential flow (ATF) pump.

8. The screening tool of claim 1, wherein the characteristic is selected from the group consisting of material type, pore size, permeability, membrane structure, and different wall thickness.

9. The screening tool of claim 1, further comprising a manifold configured to support the plurality of filter modules.

10. The screening tool of claim 9, wherein the manifold comprises first and second end caps for supporting respective first and second ends of each of the plurality of filter modules.

11. The screening tool of claim 1, further comprising a screening tool outlet comprising a reducer portion including a plate portion having a plurality of outlet fittings coupled thereto, each of said plurality of outlet fittings configured to directly engage the outlet of a separate one of said plurality of filter modules such that feed material flows directly from a respective outlet of each of the plurality of filter modules through the respective outlet fittings, wherein the screening tool outlet further comprises a single outlet coupled to the reducer portion of the screening tool outlet for receiving fluid therethrough from the plurality of outlet fittings.

12. The screening tool of claim 1, wherein the fittings of the screening tool inlet are selected from the group consisting of triclamp fittings, and luer fittings.

* * * * *